(12) United States Patent
Yasuda et al.

(10) Patent No.: US 6,764,217 B2
(45) Date of Patent: Jul. 20, 2004

(54) X-RAY DIAGNOSIS APPARATUS

(75) Inventors: Mitsunori Yasuda, Kyoto (JP); Satoru Ohishi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 184 days.

(21) Appl. No.: 09/984,530

(22) Filed: Oct. 30, 2001

(65) Prior Publication Data

US 2002/0090058 A1 Jul. 11, 2002

(30) Foreign Application Priority Data

Oct. 30, 2000 (JP) ........................................ 2000-330534
Dec. 22, 2000 (JP) ........................................ 2000-390987

(51) Int. Cl.⁷ ................................................ A61B 6/08
(52) U.S. Cl. ......................... 378/205; 378/62; 378/196
(58) Field of Search ............................. 378/4, 205, 62, 378/16, 20, 196, 195, 162, 21, 15

(56) References Cited

U.S. PATENT DOCUMENTS 5,820,553 A * 10/1998 Hughes ...................... 600/426
5,841,830 A * 11/1998 Barni et al. .................. 378/15
5,995,581 A * 11/1999 Ozaki .......................... 378/20
6,379,041 B1 * 4/2002 Schuetz et al. ............. 378/205

* cited by examiner

Primary Examiner—Craig E. Church
Assistant Examiner—Irakli Kiknadze
(74) Attorney, Agent, or Firm—Oblon, Spivak, McClelland, Maier & Neustadt, P.C.

(57) ABSTRACT

An X-ray diagnosis apparatus includes an X-ray tube, an imaging system which detects X-rays emitted from the X-ray tube and transmitted through an object to be examined and generates X-ray image data, an arm which supports the X-ray tube and the imaging system, an arm support mechanism which rotatably and movably supports the arm, and a bed which holds the object between the X-ray tube and the imaging system. This X-ray diagnosis apparatus further includes a three-dimensional image generating unit which generates three-dimensional image data from volume data concerning the object, a display unit which displays the three-dimensional image data, an input device which designates an interest point on the displayed three-dimensional image data, and a controller which controls at least one of the arm support mechanism and the bed, such that the center of the X-ray image data generated by the imaging system is positioned on a portion of the object which substantially corresponds to the designated interest point.

16 Claims, 11 Drawing Sheets

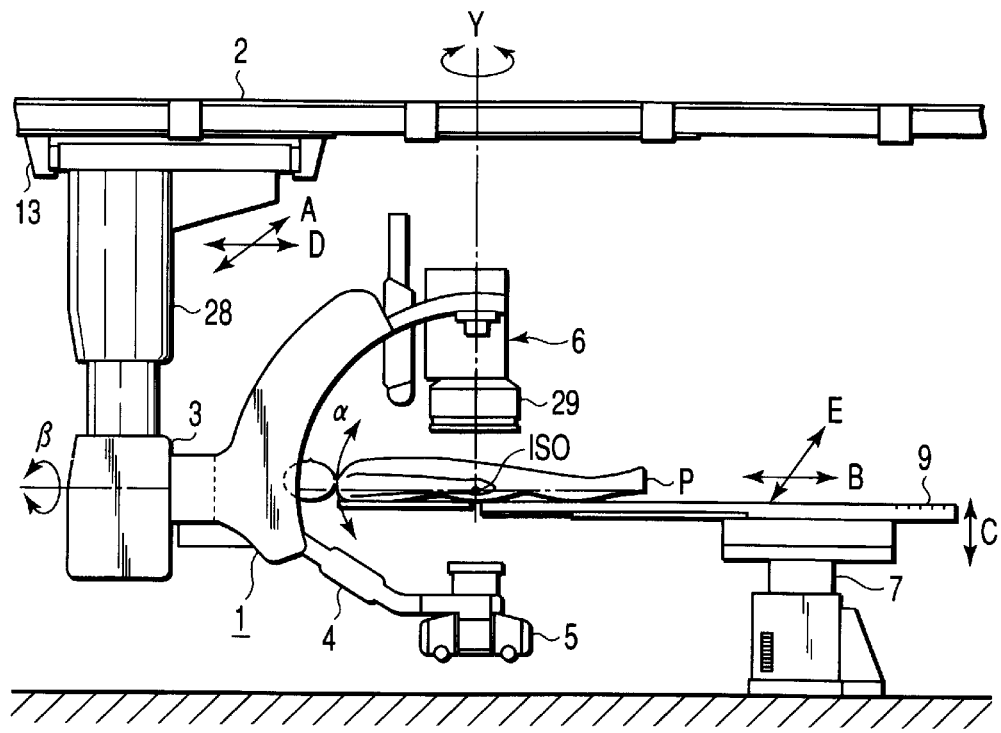
F I G. 2
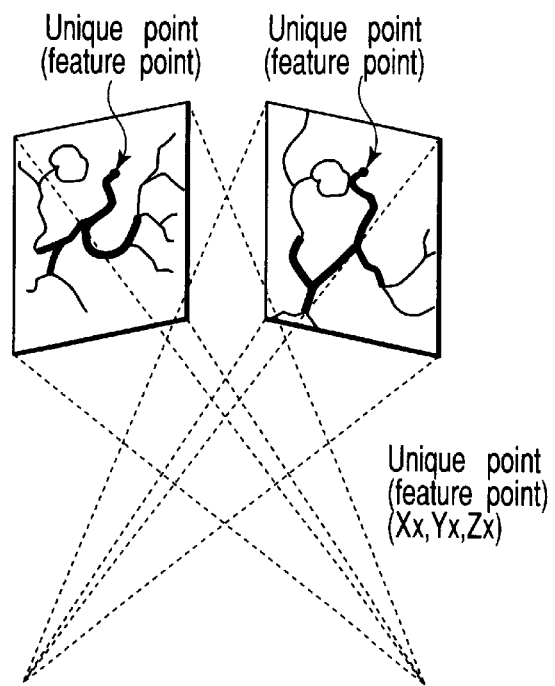
F I G. 3

$(x1, y1, z1) = \vec{Ax} \cdot t + (e0, g0, f0) = (ax, bx, cx) \cdot t + (e0, g0, f0)$
$-\infty \leq t \leq \infty$ $(x, y, z) = \vec{Aa} \cdot t + (ea, ga, fa) = (aa, ba, ca) \cdot t + (ea, ga, fa)$
$(x, y, z) = \vec{Ab} \cdot t + (eb, gb, fb) = (ab, bb, cb) \cdot t + (eb, gb, fb)$

X-RAY DIAGNOSIS APPARATUS

CROSS-REFERENCE TO RELATED APPLICATIONS

This application is based upon and claims the benefit of priority from the prior Japanese Patent Applications No. 2000-330534, filed Oct. 30, 2000, and No. 2000-390987, filed Dec. 22, 2000, the entire contents of which are incorporated herein by reference.

BACKGROUND OF THE INVENTION

1. Field of the Invention

The present invention relates to an X-ray diagnosis apparatus including a mechanism capable of supporting an X-ray tube and an imaging system in arbitrary positions so that the imaging direction can be freely changed.

2. Description of the Related Art

In X-ray diagnoses, particularly in angiography of an object to be examined, a mechanism for holding, e.g., a C- or U-shaped arm is used. An X-ray tube and an imaging system are attached to this C-arm. The imaging system is composed of an image intensifier, optical system, and TV camera.

The C-arm is supported by the support mechanism so as to be rotatable around three perpendicular axes crossing one another and to be slidable along two perpendicular axes. Accordingly, an object to be examined can be imaged from an arbitrary position in an arbitrary direction.

In advancing a catheter to a morbid portion of a blood vessel under fluoroscopy of an angiographic image, an operator can better understand the blood vessel in which the catheter is to be advanced if the blood vessel is separated from other blood vessels around it. However, when the configuration (blood vessel structure) of blood vessels is complicated as in the case of cerebral blood vessels, a blood vessel in which a catheter is to be advanced overlaps other blood vessels without being separated from them. This often makes an operator unable to well understand the blood vessel of interest.

Accordingly, to find an imaging direction along which blood vessels overlap little and an operator can better understand a blood vessel in which a catheter is to be advanced, angiography must be performed several times by changing the imaging position and imaging direction. Unfortunately, this cannot be performed in reality because a large amount of contrast agent must be injected into an object to be examined to cause side effects and the object undergoes a large amount of X-ray exposure. Therefore, an operator must manually perform operation with a blood vessel in which a catheter is to be advanced not separated from other blood vessels.

In this case, it is very difficult for the operator to advance the catheter to a morbid portion to be cured, resulting in a prolonged examination time and operation time. This increases the burdens on the patient and on the operator.

The following problem also arises. In a certain conventional imaging method, the contrast of a blood vessel is emphasized by injecting a contrast agent into an object to be examined. An X-ray diagnosis apparatus suited to this imaging method is generally called an "angiographic apparatus". This angiographic apparatus allows the insertion of a catheter into an object to be examined under X-ray fluoroscopy. In addition, imaging (so-called "bolus chase" imaging) which chases the flow of a contrast agent can be performed by moving the C-arm during the imaging.

In this X-ray diagnosis apparatus, the work of setting the C-arm in a position optimum for an interest portion (e.g., a morbid portion) inside an object to be examined is important. Conventionally, an operator always performs this work while monitoring a fluoroscopic image. Since, however, a fluoroscopic image is used to determine the imaging position, an object to be examined is continuously exposed to X-rays while the bed and the C-prm are moved and positioned. That is, the work of positioning increases the exposure dose of an object to be examined.

This problem is particularly serious in multi-direction X-ray imaging. That is, this multi-direction X-ray imaging requires the positioning work as described above in each and every direction in principle, so the exposure dose of an object to be examined increases accordingly.

To eliminate this abuse, positioning is sometimes performed in accordance with the memorized results of fluoroscopy performed within short time periods. However, confirmation using a fluoroscopic image is again necessary. This decreases the exposure dose "reducing" effect. It is well possible that no satisfactory result is obtained by one-time positioning. As a consequence, X-ray fluoroscopy, stop of the fluoroscopy, and positioning are sometimes repeatedly performed. In a case, not only the inspection time is prolonged but also the exposure dose is increased instead of being reduced.

This problem applies to the setting of so-called X-ray irradiation conditions. The X-ray irradiation conditions include the tube voltage and tube current (filament current) of an X-ray tube, the irradiation time, and the like. These X-ray irradiation conditions are set for each inspection in accordance with the physical constitution of an object to be examined and with a portion to be imaged. Similar to the positioning, the X-ray irradiation conditions are determined under X-ray fluoroscopy.

BRIEF SUMMARY OF THE INVENTION

It is an object of the present invention to shorten the time required for positioning and reduce the exposure dose in an X-ray diagnosis apparatus.

According to an aspect of the present invention, an X-ray diagnosis apparatus comprises an X-ray tube, an imaging system which detects X-rays emitted from the X-ray tube and transmitted through an object to be examined and generates X-ray image data, an arm which supports the X-ray tube and the imaging system, an arm support mechanism which rotatably and movably supports the arm, and a bed which holds the object between the X-ray tube and the imaging system. This X-ray diagnosis apparatus further comprises a three-dimensional image generating unit which generates three-dimensional image data from volume data concerning the object, a display unit which displays the three-dimensional image data, an input device which designates an interest point on the displayed three-dimensional image data, and a controller which controls at least one of the arm support mechanism and the bed, such that the center of the X-ray image data generated by the imaging system is positioned on a portion of the object which substantially corresponds to the designated interest point.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention and, together with the generation description given above and the detailed description of the preferred embodiments given below, serve to explain the principles of the invention.

FIG. 2 is a view showing the structure of a gantry of the X-ray diagnosis apparatus according to the embodiment;

FIG. 3 is a view showing a unique point designated on X-ray projected images in two directions;

DETAILED DESCRIPTION OF THE INVENTION

An embodiment of an X-ray diagnosis apparatus according to the present invention will be described below with reference to the accompanying drawing.

(First Embodiment)

Figure 1:
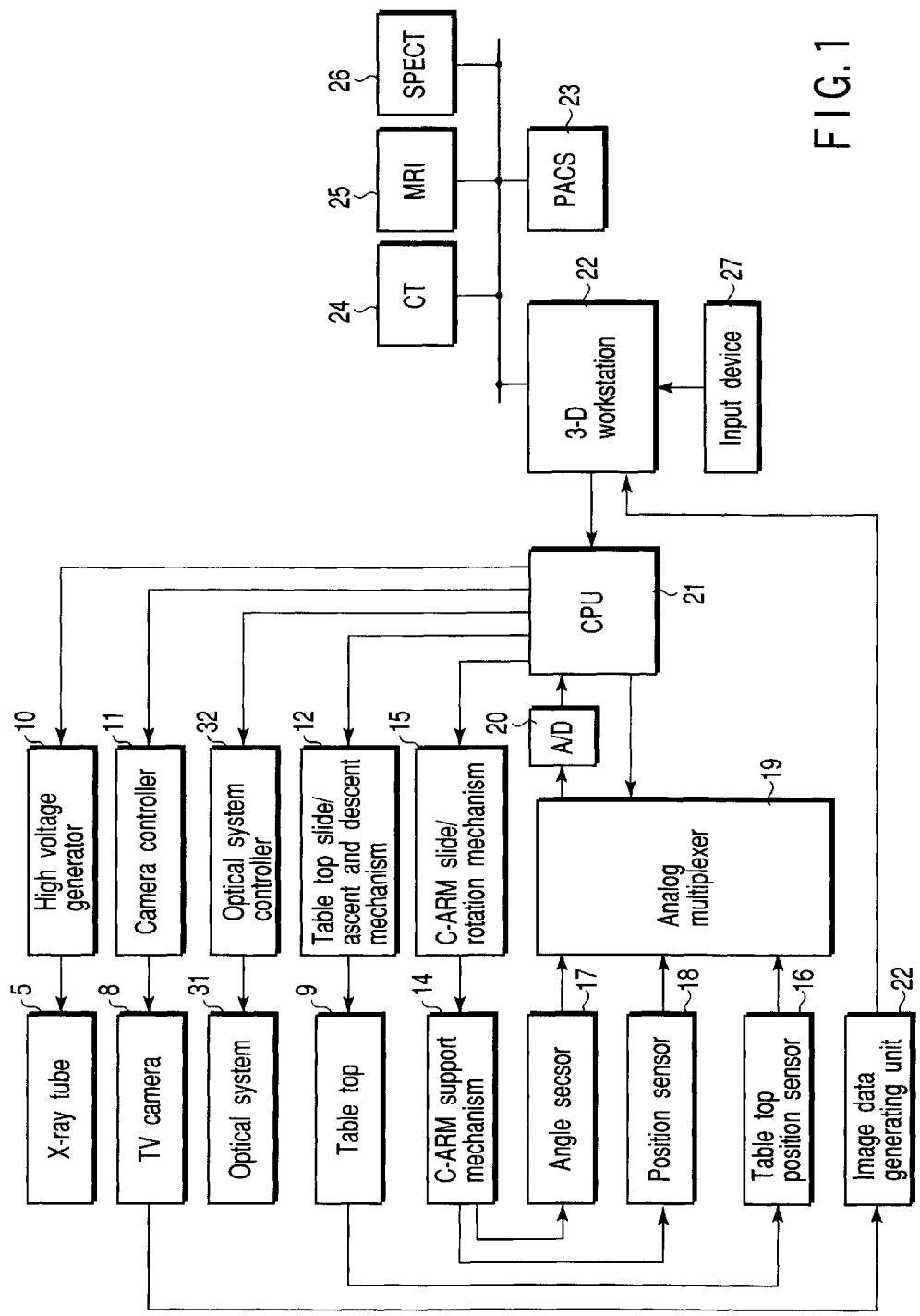
FIG. 1 is a block diagram showing the main components of an X-ray diagnosis apparatus according to an embodiment of the present invention.

FIG. 1 is a functional block diagram of the major parts of the X-ray diagnosis apparatus of this embodiment. FIG. 2 shows the structure of this X-ray diagnosis apparatus. An X-ray tube 5 and an imaging system 6 are attached to the two ends of a C-arm 4. The X-ray tube 5 generates X-rays when applied with a high voltage (tube voltage) from a high voltage generator 10. The imaging system 6 includes an image intensifier (I.I.) 29, optical system 31, and TV camera 8. The I.I. 29 converts X-rays transmitted through a patient P into an optical image. The optical system 31 guides the output optical image from the I.I. 29 to the TV camera 8. The TV camera 8 converts this optical image into an electrical signal under the control of a camera controller 11. The optical system 31 has a zoom lens in order to form the output optical image from the I.I. 29 onto the imaging surface of the TV camera 8 at an arbitrary magnification under the control of an optical system controller 32.

The imaging system 6 can be constructed by a flat panel detector. Flat panel detectors are classified into an indirect conversion type and a direct conversion type. In the indirect conversion type, X-rays are converted into light by a phosphor such as a scintillator, and this light is then converted into electric charge by a photoelectric conversion element such as a photodiode. The direct conversion type uses a so-called photoconduction phenomenon in which electron-hole pairs are generated in a semiconductor by X-rays and move to the electrode. Either type of flat panel detector can be used.

In imaging, the patient P placed on a table top (catheter table) 9 of a bed 7 is positioned between the X-ray tube 5 and the imaging system 6. The bed 7 has a table top slide/ascent and descent mechanism 12 for sliding the table top 9 forward and backward (an arrow B) and from side to side (an arrow E), and ascending and descending the table top 9 vertically (an arrow C).

To be able to freely change the imaging direction of the patient P, the C-arm 4 is slidably and rotatably (an arrow $\alpha$) held by an arm holder 1, the arm holder 1 is rotatably (an arrow $\beta$) held by a holder base 3, and the imaging system 6 is axially rotatably (an arrow $\gamma$) held by the C-arm 4. The rotating axis of the arrow $\gamma$ matches the X-ray bundle central axis (imaging central axis). The rotating axes of the arrows $\alpha$ and $\beta$ are perpendicular to the rotating axis of this arrow $\gamma$, and the rotating axes of these arrows $\alpha$ and $\beta$ are perpendicular to each other. Also, these three perpendicular rotating axes cross one another at one point (iso center ISO).

Since the three perpendicular rotating axes thus cross one another at the iso center ISO, a portion positioned in this iso center ISO is fixed to the center of an image no matter how the C-arm 4 rotates.

The holder base 3 is suspended from a ceiling base 28. This ceiling base 28 is supported, to be slidable along arrows A and D, by two systems of rails 2 and 13 laid on the ceiling to be perpendicular to each other. By freely combining the slides in the directions of these arrows A and D and the slides, ascent, and descent in the directions of the arrows B, C, and E of the table top 9, the position of the iso center ISO with respect to the patient P can be freely changed. Note that the members 1, 2, 3, 13, and 28 for holding the C-arm 4 are called a C-arm support mechanism 14. These rotations and slides of the C-arm support mechanism 14 are driven by a C-arm slide/rotation mechanism 15.

A sensor 16 composed of a rotary encoder and the like senses the position (B) and the height (C) of the table top 9. A sensor 17 composed of a rotary encoder and the like senses the rotational angles ($\alpha$, $\beta$, and $\gamma$) of the three perpendicular axes of the C-arm 4. A sensor 18 composed of a rotary encoder and the like senses the positions (A and D) of the C-arm 4. These sensor outputs are supplied to a CPU 21 via an analog multiplexer 19 and an A/D converter 20. The CPU 21 controls changes in the positions and angles on the basis of these sensor outputs.

An X-ray image signal output from the TV camera 8 is loaded into an image data generating unit 22, converted into X-ray image data corresponding to a standard such as NTSC, and displayed on a display (not shown). This image data generating unit 22 also has a function of reconstructing volume data (3D data) pertaining to a specific portion, in this embodiment a blood vessel, on the basis of X-ray image data obtained in a plurality of directions.

A three-dimensional workstation 22 is connected to the CPU 21. This three-dimensional workstation 22 is supplied with X-ray image data generated by the image data generating unit 22, and with volume data pertaining to the same specific portion, in this embodiment a blood vessel, of the same patient as the X-ray image data.

The volume data is supplied from the image data generating unit 22 or an external apparatus. This external apparatus is a modality capable of generating volume data. Examples are an X-ray computer tomography apparatus (X-ray CT) 24, a magnetic resonance imaging apparatus (MRI) 25, and a single photon emission CT (SPECT) 26. The external apparatus can also be a picture archiving and communication system (PACS) 23 which archives volume data generated by these modalities.

The three-dimensional workstation 22 has a function of generating three-dimensional image data having depth information from the volume data by using an arbitrary method designated from maximum intensity projection (MIP), integral projection method, surface display method, and volume rendering method by the user. This three-dimensional image data is displayed as a three-dimensional image on the display of the three-dimensional workstation 22. The operator operates an input device 27 to designate an internal morbid portion (interest point) of the patient on the three-dimensional image. Accordingly, the C-arm 4 so moves that the iso center ISO is positioned on or near the interest point. To this end, the coordinates of the interest point designated on the three-dimensional image must be converted into coordinates on the coordinate system unique to the X-ray diagnosis apparatus. This coordinate conversion is done by the three-dimensional workstation 22.

In accordance with the coordinates converted by the three-dimensional workstation 22, the CPU 21 aligns the iso center ISO with the interest point by freely combining the slides of the arrows A, B, C, D, and E. The morbid portion (interest point) is always positioned in the image center no matter how the imaging direction is changed by rotating the C-arm 4 along the arrows $\alpha$, $\beta$, and $\gamma$. In changing the imaging direction, therefore, the operator need not perform any operations concerning the slides of the arrows A, B, C, D, and E. That is, the operator can devote himself or herself to operations concerning the rotations of the arrows $\alpha$, $\beta$, and $\gamma$. This can increase the speed and efficiency of the work, shorten the work time, and reduce the exposure dose. Details of this process of aligning the iso center ISO with an internal morbid portion (interest point) of a patient will be described below.

Volume data of a portion including a morbid portion (interest point) of a patient is prepared by imaging performed beforehand, and supplied to the three-dimensional workstation 22. This volume data is generated by the image data generating unit 22 or an external apparatus.

When volume data generated by an external apparatus is used, the coordinate system of the X-ray diagnosis apparatus and the coordinate system of the volume data must be matched, although this processing is unnecessary when volume data generated by the image data generating unit 22 is used. The coordinate system of the volume data is basically inconsistent with that of the X-ray diagnosis apparatus. Hence, a so-called coordinate calibration process of matching the two coordinate systems is necessary.

That is, as shown in FIG. 3, a portion including the morbid portion (interest point) of the patient is imaged in two or more directions by the X-ray diagnosis apparatus. The two X-ray image data in different imaging directions obtained by this imaging are displayed on the display of the three-dimensional workstation 22. The operator operates the input device 27 to designate a point (unique point) on a clinically unique portion on each of these two X-ray images. This unique point is preferably designated on a portion which is clinically unique and easy to view.

On the basis of the imaging positions and directions and the coordinates of the unique point on each of the two X-ray images, the three-dimensional workstation 22 calculates the three-dimensional coordinates $(x_x, y_x, z_x)$ of the unique point on the coordinate system of the X-ray diagnosis apparatus.

Figure 4:
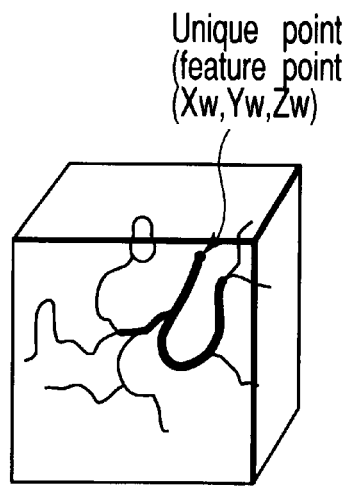
FIG. 4 is a view showing a unique point designated on a 3D image.

Next, a 3D image is displayed on the display of the three-dimensional workstation 22. On this 3D image, a unique point is designated by the operator or automatically designated by image processing, on the same clinically unique, readily viewable portion as described above (FIG. 4).

It is also possible to project the volume data in two directions and designate a unique point on the two projected images. Alternatively, a projected image is generated only in one direction, and a unique point is designated on this projected image. The value of the volume data is tracked from this point along the direction of depth (projecting direction). A point at which this value exceeds a preset threshold value corresponding to the clinically unique point is regarded as a unique point, and its three-dimensional coordinates are calculated.

The three-dimensional coordinates $(x_x, y_x, z_x)$ on the X-ray image and the three-dimensional coordinates $(x_w, y_w, z_w)$ of the unique point on the 3D image represent the coordinates of points on the same portion. The three-dimensional workstation 22 calculates a vector shift $(x_x-x_w, y_x-y_w, z_x-z_w)$ between these two coordinate points $(x_x, y_x, z_x)$ and $(x_w, y_w, z_w)$. On the basis of this vector shift $(x_x-x_w, y_x-y_w, z_x-z_w)$, the coordinates of a certain point (an interest point such as a morbid portion) on the volume data can be converted into coordinates on the coordinate system of the X-ray diagnosis apparatus. That is, the coordinates of a certain point on the volume data can be converted by shifting into coordinates on the coordinate system of the X-ray diagnosis apparatus.

Figure 5:
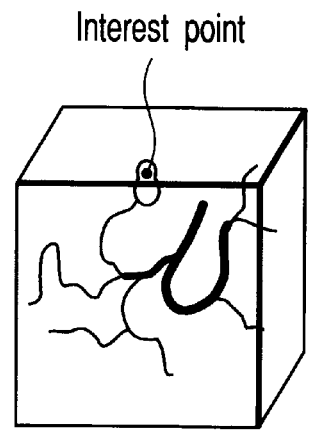
FIG. 5 is a view showing an interest point (a morbid portion to be cured) designated on a 3D image.

Subsequently, positioning of the iso center ISO is performed. First, as shown in FIG. 5, a 3D image is displayed on the display of the three-dimensional workstation 22, and the operator designates an interest point (a morbid portion to be cured) on this 3D image by using the input device 27. As in the designation of a unique point, this operation is not limited to the designation of an interest point on a 3D image. That is, it is also possible to generate projected images in two directions and designate an interest point on the two projected images. Alternatively, a projected image is generated only in one direction, and an interest point is designated on this projected image. The value of 3D data is tracked from this point along the direction of depth (projecting direction). A point at which this value exceeds a preset threshold value corresponding to a morbid portion is regarded as an interest point on the 3D data, and its three-dimensional coordinates are calculated.

Figure 6:
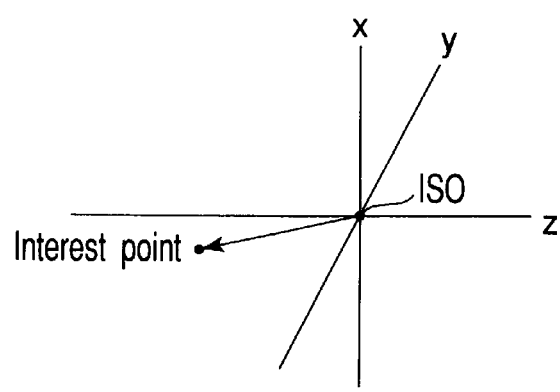
FIG. 6 is a view showing the moving vector of an iso center with respect to the interest point.

The coordinates of this interest point are converted into coordinates on the coordinate system of the X-ray diagnosis apparatus, on the basis of the already calculated vector shift $(x_x-x_w, y_x-y_w, z_x-z_w)$. A moving vector of the iso center ISO with respect to the coordinate points of this interest point is calculated (FIG. 6).

This moving vector data is supplied from the three-dimensional workstation 22 to the CPU 21. In accordance with this moving vector data, the CPU 21 moves and aligns the iso center ISO with the internal morbid portion (interest point) of the patient by freely combining the slides of the arrows A, B, C, D, and E. Consequently, the morbid portion (interest point) is always positioned in the image center no matter how the imaging direction is changed by arbitrarily rotating the C-arm 4 along the arrows α, β, and γ. This particularly increases the efficiency of the operation of changing the imaging direction.

The magnification of a 3D image is determined by the geometric positional relationship between the visual point and projection surface set when this 3D image is generated and the region center (origin) of 3D data. While the iso center is aligned with the interest point, the optical system controller 32 sets the magnification of the optical system 31, or, the image data generating unit 22 performs enlargement image processing for an X-ray image obtained by the X-ray diagnosis apparatus. Consequently, the X-ray image obtained by the X-ray diagnosis apparatus can be displayed at the same magnification as the 3D image.

If the position and direction of the C-arm 4 are already fixed in order to, e.g., ensure a catheter operation space for an operator, only the table top 9 is sometimes slid back and forth (B), from side to side (E), and vertically (C) to align the iso center with an internal morbid portion (interest point) of a patient.

When this is the case, the internal morbid portion (interest point) of the patient can sometimes be simply positioned in the image center without being aligned with the iso center. In this case, the interest point need only be positioned on the X-ray bundle central axis from the X-ray tube 5 to the I.I. Since this reduces the moving amount by one axis, the moving distance can be shortened.

Whether to align the interest point with the iso center or to position the interest point on the X-ray bundle central axis, i.e., which mode is to be chosen, is preset or selected by an operator whenever he or she performs operation.

In the above description, the slides of the arrows A, B, C, D, and E are freely combined to align the interest point with the iso center or to position the interest point on the X-ray bundle central axis. However, this can also be realized by only the slides of the table top 9 in the directions of the arrows B, C, and E, or the slides of the C-arm 4 in the directions of the arrows A and D. This selection of the slides can also be preset or done by an operator whenever he or she performs operation.

In the above explanation, to align the interest point with the iso center or to position the interest point on the X-ray bundle central axis, the slides of the arrows A, B, C, D, and E are automatically performed under the control of the CPU 21. However, the necessary moving directions and moving distances can also be displayed on the display unit. In accordance with the displayed moving directions and moving distances, an operator manually operates the apparatus by freely combining the slides of the arrows A, B, C, D, and E. In this way, the operator can align the interest point with the iso center or position the interest point on the X-ray bundle central axis.

(Second Embodiment)

Figure 7:
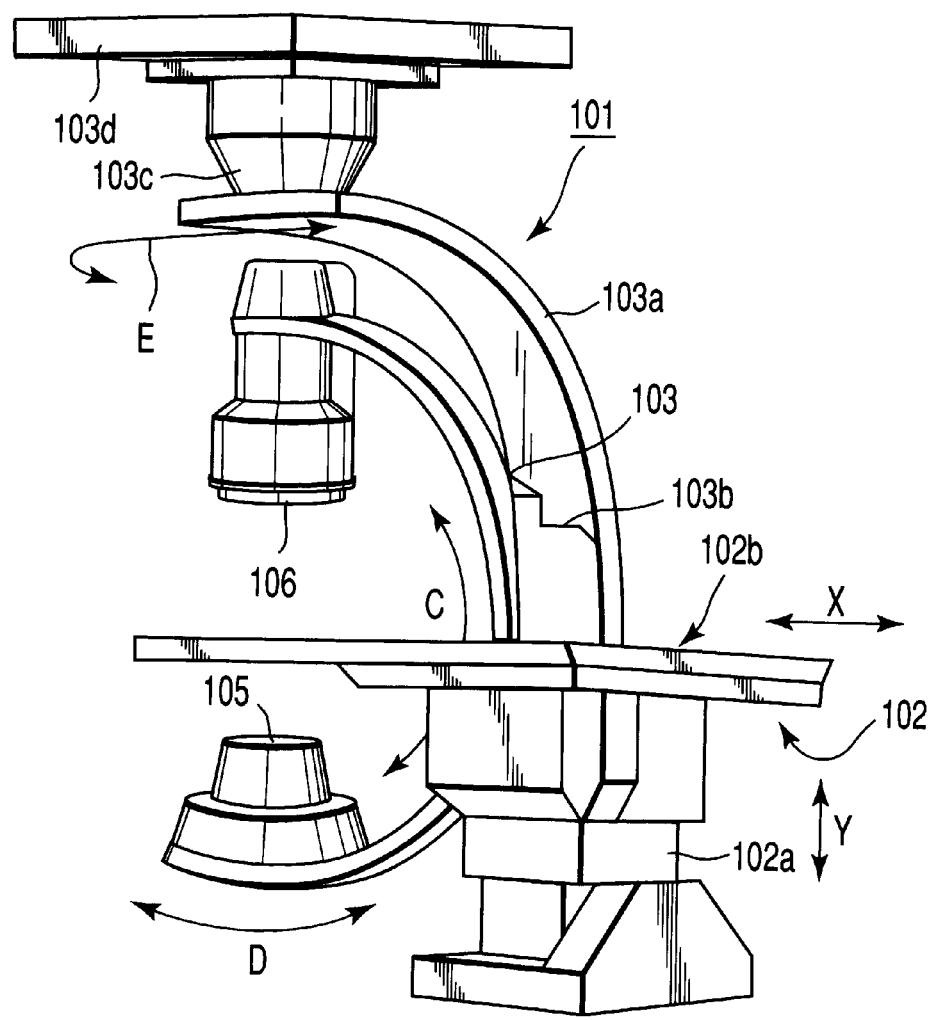
FIG. 7 is a schematic view showing the arrangement of an angiographic apparatus according to the second embodiment.
Figure 8:
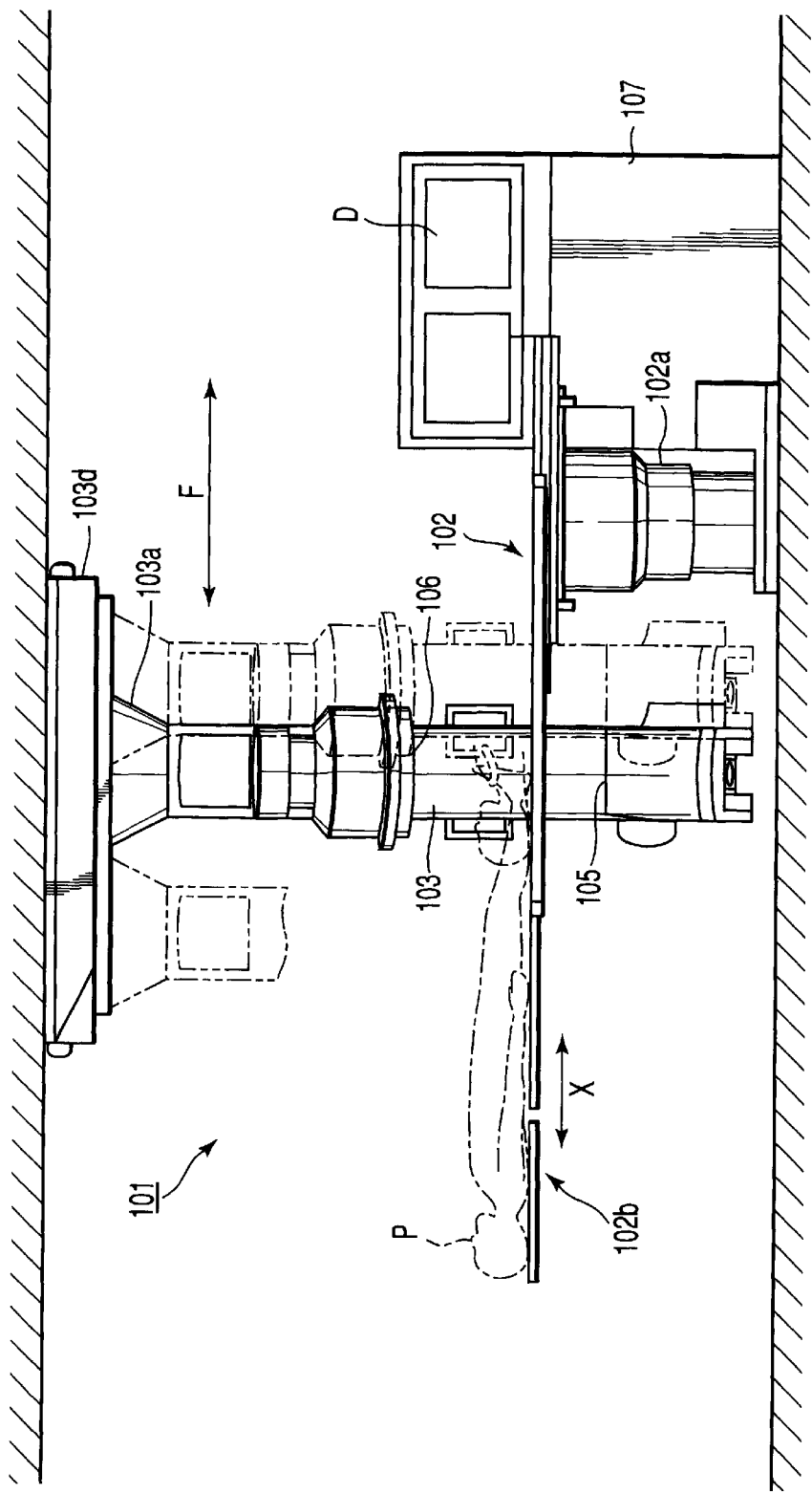
FIG. 8 is a side view of the angiographic apparatus shown in FIG. 7.

FIG. 7 is a schematic view showing the whole construction of an X-ray diagnosis apparatus according to the second embodiment. FIG. 8 is a side view of this X-ray diagnosis apparatus. In this embodiment, an "X-ray diagnosis apparatus" will be referred to as an "angiographic apparatus".

Referring to FIGS. 7 and 8, an angiographic apparatus 101 includes a bed 102 and a C-arm (support member) 103. The bed 102 has a table top 102b on which a patient P is placed, and a stand 102a. An X-ray tube 105 is mounted on one end of the C-arm 103, and an X-ray detector 106 is mounted on the other end.

Figure 10:
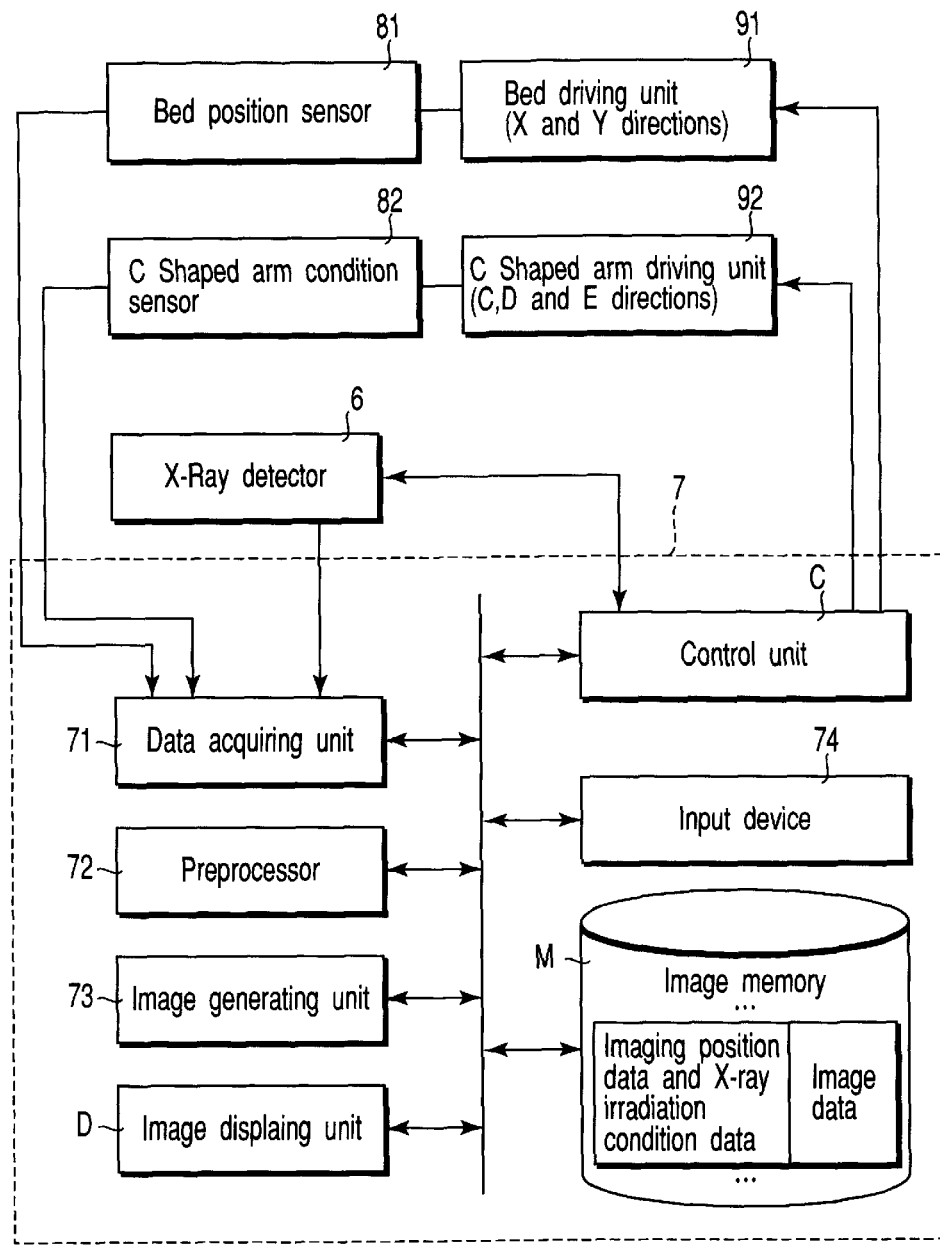
FIG. 10 is a block diagram showing the electrical configuration of the angiographic apparatus shown in FIG. 7.

As shown in FIG. 8, this angiographic apparatus 101 has an image processor 107 in addition to the bed 102 and the C-arm 103. This image processor 107 includes an image generating unit 73, an image displaying unit D, and the like (FIG. 10). The angiographic apparatus 101 having these components can allow a doctor to perform an operation or inspection, such as the insertion of a catheter into the patient P, and, in parallel with this operation or inspection, can acquire X-ray images pertaining to angiography.

As shown in FIGS. 7 and 8, the bed 102 has a moving mechanism accommodated in the stand 102a to move the table top 102b in the longitudinal direction (body axis direction), and an elevating mechanism accommodated in the stand 102a to vertically move the table top 102b. This bed 102 also includes a power source (not shown) which allows the vertical movement of the stand 102a and the movement in the body axis direction (and in a direction perpendicular to the body axis direction) of the table top 102b. These components construct a bed driving unit (91 in FIG. 10). In addition, a bed position sensor (81 in FIG. 10) senses the moving amount of the table top 102b or the like of the bed 102.

Note that the bed 102 can be either fixed on the floor or moved together with the stand 102a. In the latter case, it is possible to install an additional power source and make the bed position sensor able to sense the moving amount of the bed movement.

The X-ray tube 105 and the X-ray detector 106 constructed by, e.g., an image intensifier (I.I.) are attached, so as to oppose each other, to one end and the other end of the C-arm 103 of the angiographic apparatus 101. The C-arm 103 is set such that these X-ray tube 105 and X-ray detector 106 sandwich the table top 102b and the patient P during X-ray imaging. Note that the state as shown in FIG. 7, i.e., the state in which a straight line connecting the X-ray focal point of the X-ray tube 105 and the imaging surface center of the X-ray detector 106 extends through the patient P in the vertical direction, will be referred to as a "normal state" hereinafter.

Although an image intensifier can be used as the X-ray detector 106 as described above, this X-ray detector 106 is not restricted to this form. As an example, a so-called "FPD (Flat Panel Detector)" is of course usable as the X-ray detector 106.

As shown in FIG. 7, the C-arm 103 is connected to an outer arm 103a via an arm holder 103b. This arm holder 103b can slide the C-arm 103 as indicated by arrows C in FIG. 7, and can also rotate the C-arm 103 as indicated by arrows D in FIG. 7, with respect to the outer arm 103a.

Figure 9A:
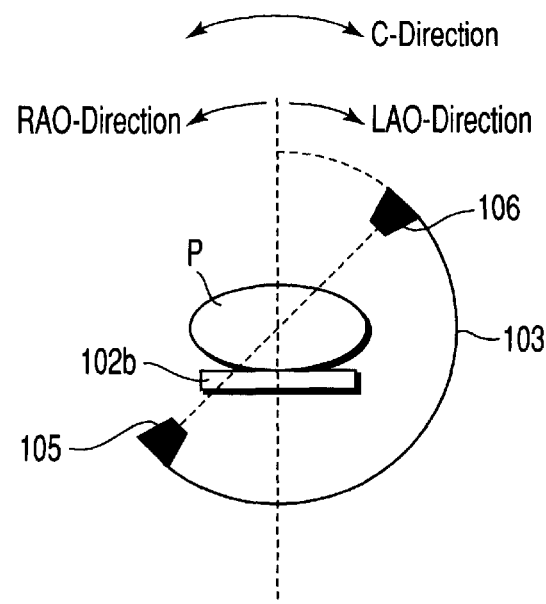
FIG. 9A is a view for explaining the posture that can be taken by a C-arm of the angiographic apparatus shown in FIG. 7 in relation to an RAO-direction or LAO-direction.
Figure 9B:
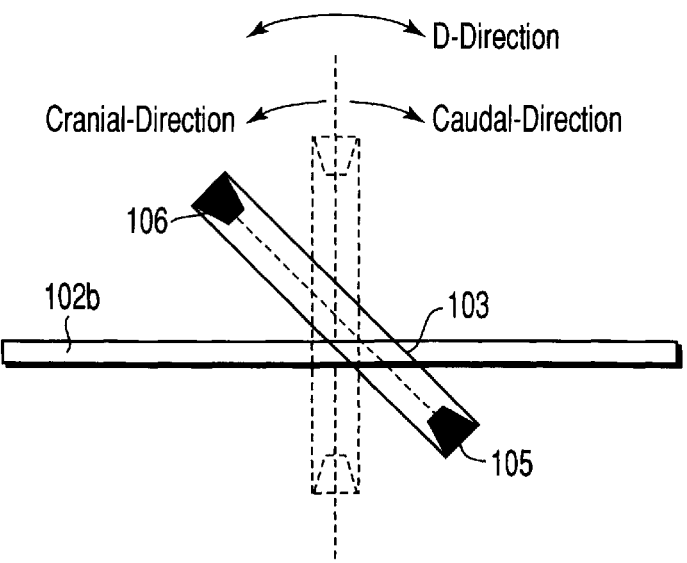
FIG. 9B is a view for explaining the posture that can be taken by the C-arm of the angiographic apparatus shown in FIG. 7 in relation to a cranial-direction or caudal-direction.

Note that the operating directions indicated by the arrows C are generally called an "LAO-direction" and an "RAO-direction". As schematically shown in FIG. 9A, the former LAO-direction is a direction in which the lower end of the C-arm 103 in the normal state extends farther from the lower surface of the table top 102b, and the upper end of the C-arm 103 is retracted from the portion above the patient P. The latter RAO-direction is the opposite direction. The operating directions indicated by the arrows D are generally called a "cranial-direction" and a "caudal-direction". As shown in FIG. 9B, the former cranial-direction is a direction in which the C-arm 103 in the normal state falls to the right (to the left in the drawing). The latter caudal-direction is the opposite direction (to the right in the drawing).

As shown in FIG. 7, one end of the outer arm 103a is rotatably attached to a support 103c on the ceiling. By this support 103c, the outer arm 103a and the C-arm 103 rotate as indicated by arrows E. In addition, as shown in FIGS. 7 and 8, the support 103c is attached to the ceiling surface via a base 103d. This base 103d moves in directions indicated by arrows F in FIG. 7 along rails (not shown). With the above construction, the "C-arm 103" can eventually move in the directions of the arrows F. Note that the C-arm 103 and the base 103d can also move close to or away from the ceiling surface, in addition to the above-mentioned movements.

A plurality of power sources for realizing the operations pertaining to the arrows C, D, E, and F described above are set in corresponding appropriate portions of the C-arm 103. These power sources construct a C shaped arm driving unit (92 in FIG. 10). The C-arm 103 further includes a C shaped arm condition sensor (82 in FIG. 10), constructed by, e.g., a potentiometer or encoder to sense the information of the angle, posture, or position in accordance with each power source of the C shaped arm driving unit. More specifically, the encoder can be a so-called absolute encoder of magnetic type, brush type, or photoelectric type. Also, the present invention does not restrict the type of rotary encoder or linear encoder.

Note that an intersection of two axes passing the centers of the rotations indicated by the arrows C and E of the C-arm 103 will be referred to as an "iso center of the C-arm 103" hereinafter. Note also that the mechanisms for realizing the movements of the C-arm 103 explained above are merely examples, so the present invention is not limited to these forms. For example, the movement in the F directions in FIG. 8 of the C-arm 103 is realized by so-called overhead traveling by which the base 103d travels along the rails laid on the ceiling. However, the movement in the F directions in FIG. 8 can also be realized by installing another member for holding the C-arm 103 on the floor surface and moving this member along the floor surface.

As shown in the block diagram of FIG. 10, the image processor comprises a data acquiring unit 71, preprocessor 72, image generating unit 73, image displaying unit D, image memory M, and the like. The data acquiring unit 71 acquires input X-ray data from the X-ray detector 106 and converts the data into a digital signal. The preprocessor 72 performs various processes such as calibration for the converted digital X-ray data. The image generating unit 73 generates an image on the basis of the results of the processes. The image displaying unit D displays the generated image. The image memory M stores the image as image data.

As shown in FIG. 10, the data acquiring unit 71 is connected to the bed position sensor 81 and the C shaped arm condition sensor 82. These sensors 81 and 82 are connected to the bed driving unit 91 and the C shaped arm driving unit 92. By the functions of these components, information (to be referred to as "imaging position information" hereinafter) concerning those positions and postures of the bed 102, table top 102b, and C-arm 103, which change in accordance with the actions of the power sources mentioned above, is acquired simultaneously with the X-ray data acquisition. Management information concerning an image generated by the image generating unit 73 contains this simultaneously acquired imaging position information of, e.g., the C-arm 103. That is, an image displayed on the image displaying unit D or image data stored in the image memory M always has imaging position information attached, which is unique to the image or the image data, as attribute information (see the block of the image memory M in FIG. 10).

This imaging position information (imaging position data file) contains data pertaining to the angles (C, D, and E) of the C-arm 103, the position (F) of the C-arm 103, the position (X) of the table top 102b, and the height (Y) of the table top 102b. The imaging position data file is stored, as it is related to an image data file, in the image memory M. The image memory M stores a plurality of image data files, and a plurality of imaging position data files are related in one-to-one correspondence with these image data files. The imaging position such as the angle of the C-arm 103 when a certain image data file is generated can be reproduced from an imaging position data file related to that image data file.

In this embodiment, when X-ray imaging is performed in a certain imaging position, information (X-ray irradiation condition data file) concerning the X-ray irradiation conditions in that imaging position, i.e., the tube voltage and tube current of the X-ray tube 105 and the X-ray irradiation time, is stored, as it is related to an image data file along with an imaging position data file, in addition to the imaging position information described above.

Furthermore, as shown in FIG. 10, the image processor 107 comprises a control unit C for controlling the driving timings of the above components (71 to 73, 80, and 81), and controlling the X-ray detector 105 and the like. The image processor 107 also has an input device 74 for transmitting the intent of the user of the apparatus to these components. In particular, the control unit C of this embodiment performs calculations for controlling the operations of the bed 102 and the C-arm 103 on the basis of the imaging position information, and controlling the operations of the bed 102 and the C-arm 103 on the basis of specification inputting for a fluoroscopic image via the input device 74, and also generates control signals and the like for actually realizing these operations (to be described in detail later). Various devices can be used as the input device 74. Examples are a keyboard, mouse, joystick, trackball, jog shuttle, and device (so-called touch pen) which can input data in direct contact with the image display screen of the displaying unit D.

The functions and effects of the angiographic apparatus 101 having the above configuration will be explained below with reference to flow charts in FIGS. 11, 12, 13, and 16. This embodiment is characterized in that the bed 102 and the C-arm 103 are positioned on the basis of an imaging position data file related to an image data file acquired by the angiographic apparatus 101, or on the basis of an input for specifying a region of interest in the corresponding image. Therefore, the explanation will focus on this respect. The former (positioning is performed using an imaging position data file) will be called a first mode, the latter (positioning is performed on the basis of an interest point designated on an image) will be called a second mode, and an item pertaining to both the first and second modes will be called a third mode. The apparatus of this embodiment is equipped with these three modes, and the modes are selectively used in accordance with designation from an operator. Note that in the first mode, a case in which X-ray irradiation conditions are automatically set, after positioning is performed, on the basis of an X-ray irradiation condition data file related to an image data file to which an imaging position data file is related, will be explained as well.

(First Mode)

In the angiographic apparatus 101 in this mode, the bed 102, the table 102b, and the C-arm 103 can be properly moved and positioned on the basis of an imaging position data file attached to an already sensed X-ray image. The "imaging position data file related to an already sensed X-ray image" can also be referred to as information concerning the positions and angles of the bed 102 and the C-arm 103 when X-ray data as a source of the X-ray image data file is acquired, or referred to as an imaging position when the X-ray image is sensed. In this first mode, the position and angle of at least one of the table top 102b, the bed 102, and the C-arm 103 are so automatically set as to be consistent with the imaging position when this X-ray image is sensed. Four patterns of the mode will be separately explained below.

(First Pattern)

Figure 11:
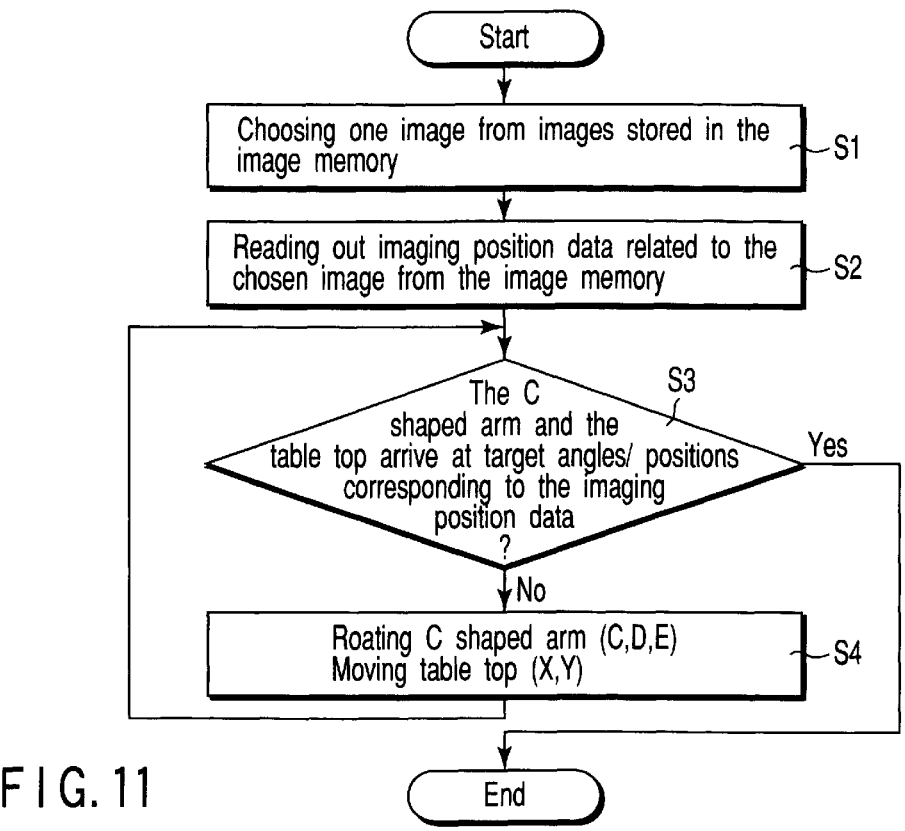
FIG. 11 is a flow chart showing the flow of a process according to the first mode of the second embodiment, by which an image stored in an image memory is selected and the angiographic apparatus is set in the same imaging position as the image.

In this first pattern, one image in the image memory M is chosen and input via the input device 74 (step S1 in FIG. 11). From an imaging position data file related to the corresponding image data file, the control unit C extracts data pertaining to the angle (the "cranial-direction" or "caudal-direction, or the "RAO-direction" or "LAO-direction) of the C-arm 103 (step S2 in FIG. 11). On the basis of this data, the C-arm 103 is moved (in this case, "rotated") toward the position indicated by the data and set in that position via the C shaped arm driving unit 92 (steps S3 and S4 in FIG. 11).

This method of use is effective in checking images of the same portion before and after an operation. That is, in this method of use an image viewed in the same direction as an image before an operation can be readily checked after the operation. This naturally allows easy confirmation of the effect of the treatment within short time periods. In other words, to check images of the same portion before and after an operation by the conventional method, the operator must set the positions of the bed 102 and the C-arm 103 again in accordance with the image sensed before the operation, while monitoring a fluoroscopic image of the patient. This first pattern eliminates this necessity. The significance of this first pattern is especially obvious when compared to the conventional method by which a fluoroscopic image must be acquired again, i.e., the patient must be exposed to X rays again.

Note that the C-arm 103 is preferably moved and positioned such that the actual movement of this C-arm 103 (step S4 in FIG. 11) is performed only while a "C-arm rotation button" (not shown) of the input device 74 is being pressed. This allows the user of the apparatus to control the progress and completion of the movement and positioning at any time, while checking the occasional movement of the C-arm 103. Consequently, it is possible to avoid inconvenience such as the occurrence of interference between this C-arm 103 and the patient P (i.e., to ensure the safety of the patient P).

(Second Pattern)

In this second pattern, a plurality of X-ray images retrieved by a keyword such as a patient name from the image memory M are displayed in the form of a list on the displaying unit D, and an operator selectively designates one desired X-ray image. An imaging position data file related to the selected image data file is read out from the image memory M. Of the readout imaging position data file, the second pattern uses information concerning the position and angle of the C-arm 103 and information concerning the position and angle of the table top 102b, i.e., uses all information (all data) configuring the imaging position data file. In this case, a control signal is transmitted to one or both of the bed driving unit 91 and the C shaped arm driving unit 92, thereby moving and positioning the table top 102b and/or the C-arm 103 (see the description in the parentheses in step S4 of FIG. 11).

This method of use is effective when, for example, a region of interest (e.g., a stenotic or occlusive region of a blood vessel, and more generally, a "morbid region"; the same shall apply hereinafter) must be inspected again while an inspection by which a plurality of images are sensed by continuously changing the position of the C-arm 103 or the like is being performed, and therefore it is necessary to reproduce the positional relationship (=the relative positional relationship between the bed 102 and the C-arm 103) which is obtained once during the continuous change. Similar to the first pattern described above, the second pattern is characterized in that no unnecessary exposure to X-rays is forced upon the patient even in a case like this.

Note that in this second pattern, as in the above-mentioned first pattern, the bed 102 and/or the C-arm 103 is preferably moved only while a "position moving button" (not shown) of the input device 74 is being pressed.

Also, while an inspection by which the position and posture of the C-arm 103 or the like are continuously changed is being executed as described above, acquired images are related to the same patient. Therefore, when the imaging position reproduction process mentioned earlier or shown in FIG. 11 is performed (i.e., when the angle of the C-arm 103 which defines the X-ray imaging angle and the relative positional relationship between the bed 102 and the C-arm 103 are reproduced as the same angle and relative positional relationship as before), the X-ray irradiation conditions at that time can be substantially the same as the X-ray irradiation conditions in the reproduced imaging position.

In a case like this, therefore, another effect different from the above one is achieved by using those X-ray irradiation conditions in the different imaging positions, which can be stored in the image memory M as they are attached to image data as described above. That is, when the imaging position reproduction process mentioned earlier or shown in FIG. 11 is performed, the corresponding X-ray irradiation conditions are preferably automatically set to be consistent with the X-ray irradiation conditions in the reproduced imaging position. This obviates the need to give the patient extra exposure to X-rays by performing X-ray irradiation condition determining fluoroscopy.

Note that an image of the first frame can be well used as an inspection image by image processing even if the X-ray irradiation conditions are slightly different. Also, images of the second and subsequent frames have almost no problem because the X-ray irradiation conditions can be set more strictly on the basis of the sensed image of the first frame.

Furthermore, the above embodiment is directly applicable if there is a mechanism (e.g., a mark on the table top or fixation of the head and the stand in the same position) which, when a designated image is related to the same patient but is not obtained in a continuous inspection (e.g., when an inspection image of the preceding day is referred to), can hold the posture of the patient in substantially the same state.

This idea can be applied to the first pattern described above and to the third and fourth patterns to be described below as well. Also, the item (=reduction of the exposure dose of the patient) described as the effect of the first and second patterns and the arrangement in which the bed 102 and/or the C-arm 103 is moved only while a certain button is being pressed completely apply to the third and fourth patterns. Accordingly, a description of this item and the like will be omitted in the third and fourth patterns.

(Third Pattern)

This third pattern is exactly the same as the first and second patterns in that an image stored in the image memory M is chosen and the C-arm 103 or the like is moved in accordance with an imaging position data file related to the chosen image data file. In this third pattern, however, an image to be chosen is composed of a plurality of images sensed while the angle of the C-arm 103 is changed.

Figure 12:
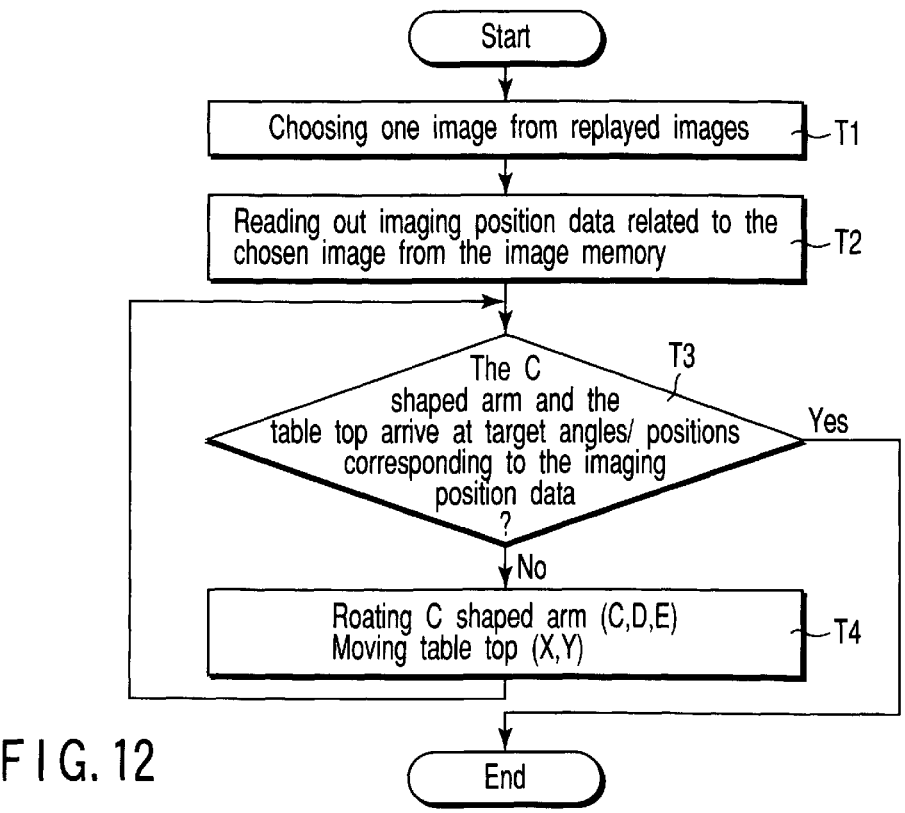
FIG. 12 is a flow chart showing the same process as in FIG. 11.

That is, while the plurality of images (moving image data) in the image memory M are replayed, one of these images is chosen via the input device 74 (step T1 in FIG. 12). This choice can be performed on the basis of a subjective criterion of the user of the apparatus, such as an "image by which a region of interest is clearly seen".

After that, from an imaging position data file related to the chosen image data, the control unit C reads out data pertaining to the angle of the C-arm 103 (step T2 in FIG. 12). On the basis of the readout data, the C-arm 103 is moved to the position indicated by the data and set in that position via the C shaped arm driving unit 92 (steps T3 and T4 in FIG. 12).

(Fourth Pattern)

The relationship of this fourth pattern to the above third pattern is exactly the same as the relationship of the second pattern to the first pattern mentioned earlier. That is, this fourth pattern differs from the third pattern in that the rotation of the C-arm 103 alone is taken into consideration in the third pattern, whereas the position and angle of the C-arm 103 and the position and height of the table top 102b are also taken into account in the fourth pattern.

That is, this fourth pattern uses all information (all data) configuring imaging position information attached to a chosen image (see the description in the parentheses in step T2 of FIG. 12). A control signal is transmitted to one or both of the bed driving unit 91 and the C shaped arm driving unit 92, and the table top 102b and/or the C-arm 103 is moved and positioned (see the description in the parentheses in step T4 of FIG. 12).

Note that in this first mode, the above four patterns can of course be separately performed and, in accordance with the progress of an inspection, two or more of these patterns can be appropriately combined.

In the first to fourth patterns described above, when imaging is to be performed for a certain patient and the positions and postures of the table top 102b, the bed 102, and the C-arm 103 are to be automatically set as substantially the same imaging position as an imaging position stored in relation to the patient, X-ray irradiation conditions during the setting can also be automatically set to be consistent with X-ray irradiation conditions in that imaging position, as described in the explanation of the second pattern. This obviates the need to give the patient unwanted exposure to X-ray.

In this case, the imaging position information and the X-ray irradiation conditions can be collectively regarded as "inspection information". This embodiment is similarly applicable to a case in which an imaging position is manually set, as well as to a case in which an imaging position is automatically set as in the first to fourth patterns described above. That is, an imaging position is manually set and, if the set imaging position is substantially consistent with a certain imaging position in stored inspection information, X-ray irradiation conditions in that imaging position are automatically set (note that the patient must be the same).

(Second Mode)

In the angiographic apparatus 101 in this second mode, under so-called "fluoroscopic imaging" in which low-dose X-rays are continuously generated from the X-ray tube 105 and processed in real time by, e.g., the X-ray detector 106 and the image generating unit 73, a fluoroscopic image (X-ray image) obtained at any time by the processing can be displayed on the image displaying unit D. In addition, on the basis of an input for specifying the position in this fluoroscopic image, the table top 102b and the C-arm 103 can be appropriately moved and positioned. This second mode has the following three methods.

(First Method)

Generally, the purpose of practicing the above fluoroscopic imaging is to check the positional relationship of a region of interest in the patient P, and to adjust the position and the like of the bed 102 and the C-arm 103 such that this region of interest is exactly positioned on a line segment connecting the X-ray tube 105 and the X-ray detector 106 of the C-arm 103, before main imaging (e.g., "bolus chase imaging") scheduled after the fluoroscopic imaging is performed.

In this first method, the above adjustment can be rapidly and efficiently performed by practicing the following process. First, as described in step U1 of FIG. 13, a region of interest in a given fluoroscopic image acquired (or currently being acquired) is specified via the input device 74. A "given" "fluoroscopic image" means that the bed 102 and the C-arm 103 are not particularly set in predetermined positions, and (therefore) an image of a region of interest is not necessarily positioned in the center of the image displaying unit D.

Figure 14:
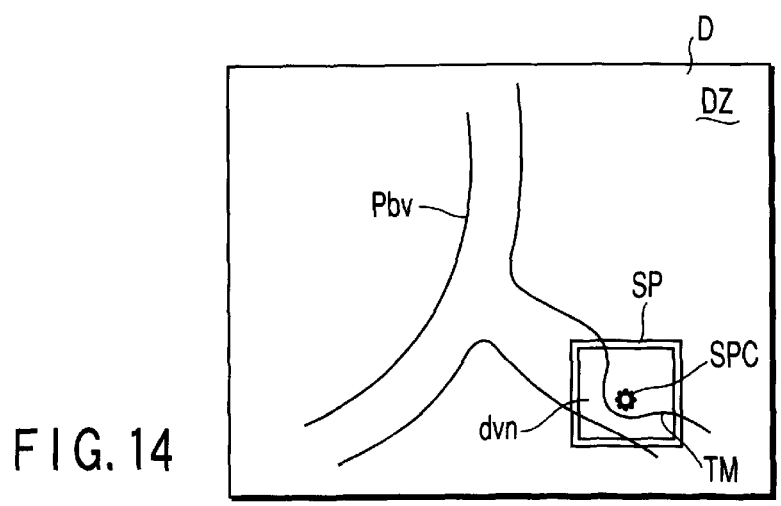
FIG. 14 is a view for explaining a display example of the fluoroscopic image and an example of the input for specifying a region of interest.

As shown in FIG. 14, for example, the input for specifying the position described above can be performed by surrounding a region of an appropriate size by the mouse or the like. Referring to FIG. 14, a fluoroscopic image DZ is an image representing a blood vessel Pdv in a part of which a tumor TM and a relevant occlusive portion dvn (=an image of a region of interest) are observed. In addition, a region SP containing the tumor TM and the occlusive portion dvn is specified by the above input.

Figure 13:
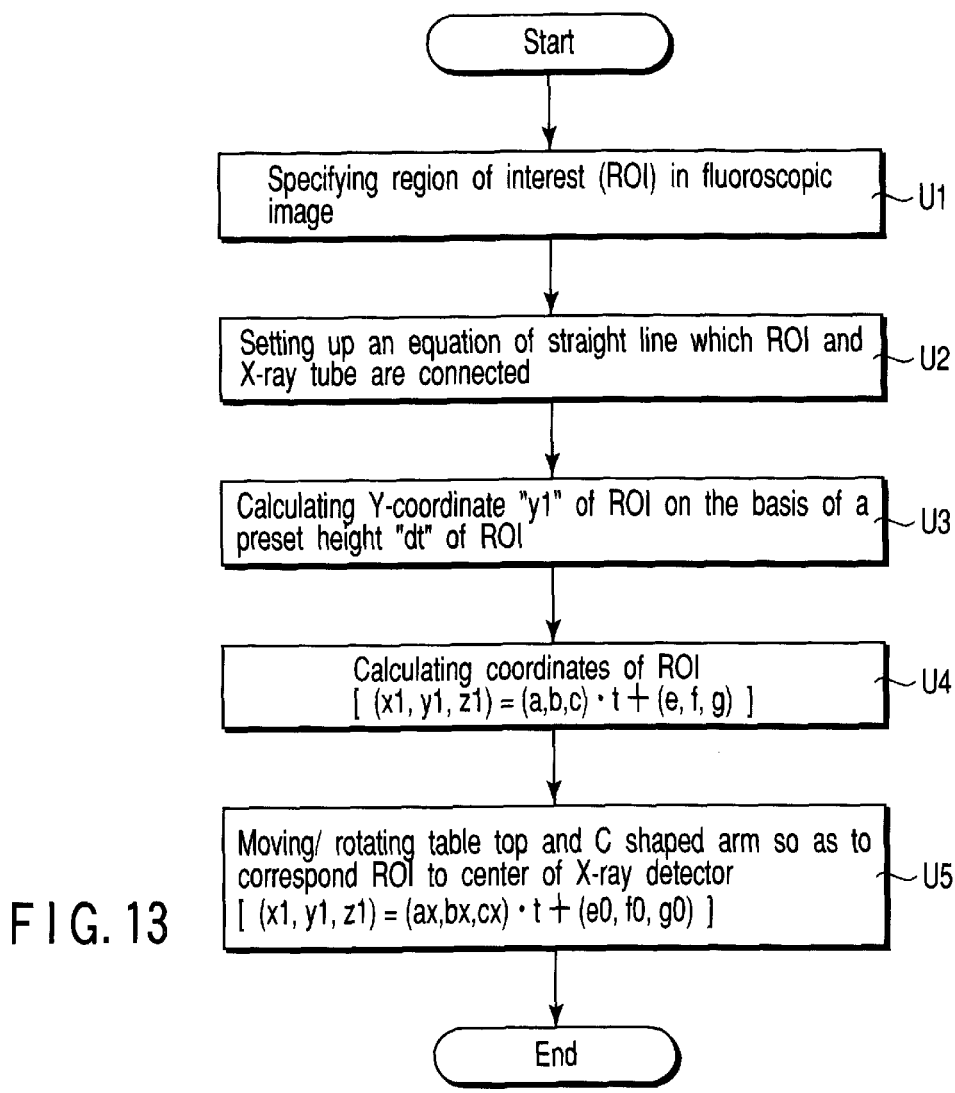
FIG. 13 is a flow chart showing the flow of a process according to the first method in the second mode of the second embodiment, by which on the basis of an input for specifying a region of interest in a fluoroscopic image, an image of this region of interest is displayed in the center of an image displaying unit.

Next, as in step U2 of FIG. 13, the control unit C checks on the basis of the above input the way the X-ray locus passing the region of interest in the patient P is expressed on a real space (=a space in which this angiographic apparatus 101 is installed). "Passing the region of interest" can be simply interpreted as "passing (a coordinate point, on the real space on the X-ray detector 106, corresponding to) a central portion SPC". The coordinate system can be the one having the iso center of the C-arm 103 as an origin. In this case, the control unit C calculates the way a straight line connecting (the coordinate point pertaining to) the central portion SPC and the X-ray focal point of the X-ray tube 105 is expressed in the coordinate system having the iso center of the C-arm 103 as an origin.

More specifically, assuming that the coordinate point, on the real space on the X-ray detector 106, corresponding to the central portion SPC is (e, f, g), and a vector connecting this coordinate point (e, f, g) and the center of the X-ray tube 105 is A=(a, b, c), the X-ray locus or straight line described above can be represented by $$(x,y,z)=A \cdot t+(e,f,g), \text{ or } (x,y,z)=(a,b,c) \cdot t+(e,f,g) \qquad (1)$$

where t is a parameter represented by $$-\infty \leq t \leq \infty \quad (2)$$

The vector A and the coordinate point (e, f, g) can be calculated on the basis of, e.g., the present position of the C-arm 103 obtained from the C shaped arm condition sensor 92, or the length (design value) of one pixel on the X-ray detector 106.

Figure 15:
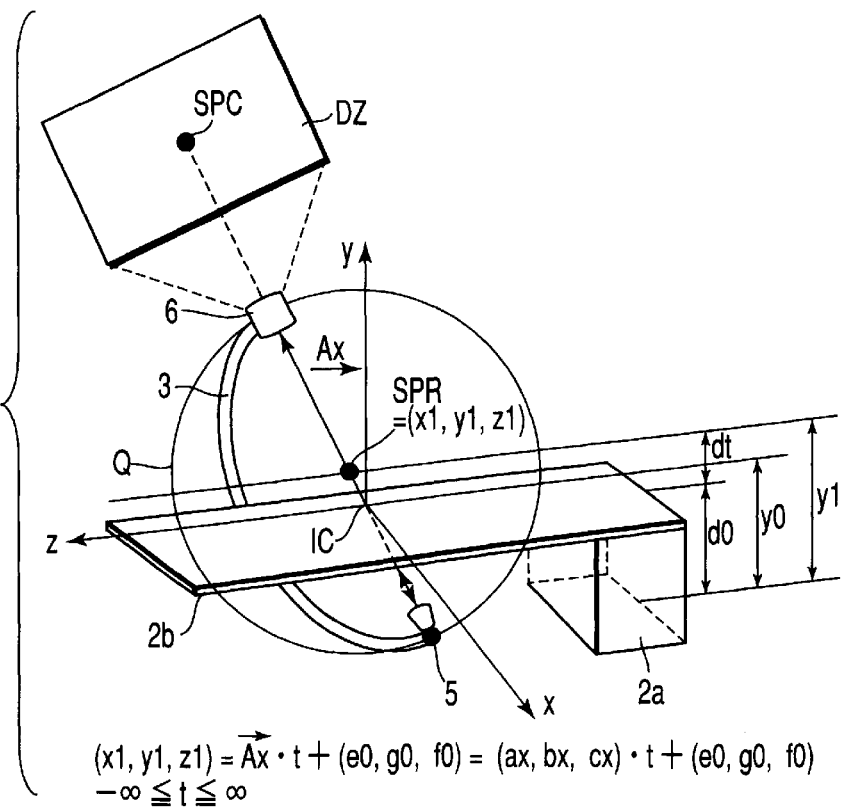
FIG. 15 is a view for explaining a three-dimensional space, X-ray locus, and the like assumed in practicing the process shown in FIG. 13.

The coordinate system is as shown in FIG. 15. Referring to FIG. 15, reference symbol SPR denotes a region of interest in the patient P; and IC, the iso center as an origin. This coordinate system is so set that the z-axis direction is consistent with the body-axis direction of the patient, the x-y plane is consistent with that section of the patient which is perpendicular to the z-axis, and the y-axis direction is consistent with the vertical direction.

Subsequent to the calculations concerning the X-ray locus, as indicated in step U3 of FIG. 13, the control unit C calculates coordinate values of the "height" position of the region of interest SPR from a preset value and the physical height of the bed 102. The "preset value" is a numerical value representing the height of the region of interest SPR from the surface of the table top 102b. This preset value can be prepared as a predetermined value beforehand. For example, when the fluoroscopic image DZ shown in FIG. 14 is an image concerning the "chest", the preset value is determined to be, e.g., "about 10 cm" from the surface of the table top 102b. Note that this preset value can be input before the processing currently being explained is started (i.e., before step U1 in FIG. 13).

The image memory M stores table data indicating correspondence between a plurality of regions (e.g., an abdomen, chest, and head) to be inspected and a plurality of heights. The image memory M can also store table data more finely indicating correspondence between portions (e.g., an internal carotid artery and middle cerebral artery) to be inspected in a region to be imaged and a plurality of heights. When the former table data is used, the table top height can be set in substantially the center of a region. When the latter table data is used, the table top height can be more precisely set in substantially the center of a portion in a region. These table data can have arbitrary specifications.

A region or portion to be inspected can be specified from data concerning a region or portion to be inspected extracted from inspection request information. The control unit C can specify a region or portion to be inspected from this inspection request information, and extracts the corresponding height (preset value) from the table data.

A region or portion to be inspected can also be selected when specification inputting is performed for an image of the region of interest SPR.

Letting dt be the preset value, a coordinate value y1 of the height of the region of interest SPR can be represented by the following equation (FIG. 15).

$$y1=dt+d0-y0 \quad (3)$$

where d0 is a value representing the physical height ($\approx$ the height of the stand 102a) of the bed 102 and is known via the bed position sensor 91, and y0 represents the height of the iso center.

Subsequently, as indicated in step U4 of FIG. 13, the control unit C confirms from equations (1) and (3) that the expression of the X-ray locus, passing the region of interest SPR, on the real space is $$(x,y1,z)=(a,b,c)\cdot t+(e,f,g) \quad (4)$$

In addition, the control unit C determines practical numerical values of the coordinate values x and y, i.e., determines the coordinate values (x1, y1, z1) of the region of interest SPR. More specifically, t=(y1−f)/b is obtained because all values (except for t) on the right-hand side of equation (4) are known and y1=b·t+f. x1 and z1 can be calculated from this t and equation (4).

Through the above processing, as indicated in step U5 of FIG. 13, the control unit C moves the position and posture of the bed 102 and/or the C-arm 103 and positions the bed 102 and/or the C-arm 103, such that a projected image of the coordinate point (x1, y1, z1) of the region of interest SPR calculated as above is positioned in the center of the X-ray detector 106 (=an image of the region of interest SPR is positioned in the center of the image displaying unit D). More specifically, assume that when this positioning is successfully completed, those coordinate values of the center of the X-ray detector 106, which indicate the position and posture of the C-arm 103 at that time are (e0, f0, g0). When this is the case, similar to equation (3) or (4), (x1, y1, z1) can be expressed by $$(x1,y1,z1)=(ax,bx,cx)\cdot t+(e0,f0,g0) \quad (5)$$

Therefore, it is only necessary to realize the movement and positioning which satisfy this equation.

In this case, however, positions and postures which can be taken by the bed 102 and the C-arm 103, i.e., final positions ($\approx$ practical values of vector Ax=(ax, bx, cx) and (e0, f0, g0) of equation (5)) of the bed 102 and the C-arm 103 in which the region of interest SPR at the coordinate point (x1, y1, z1) can be projected onto the center of the X-ray detector 106, or practical procedures of movement to these positions, are infinite in principle. Accordingly, it is preferable to impose certain limitations when the movement and positioning described above are practiced.

For example, as shown in FIG. 15, assuming a sphere Q which has the origin IC as its center and on the surface of which the coordinate point (e, f, g) is present, the position of (e0, f0, g0) is determined only on the surface of this sphere Q. That is, in this method, a limitation is imposed in that "the point (e0, f0, g0) is present on the surface of the sphere Q".

A practical method of calculating the root is as follows. For example, for the coordinate values (ec, fc, gc) of the center of the X-ray detector 106 with respect to the present posture of the C-arm 103 and the intersection (ex, fx, gx) (x=1, 2, . . . , n) of a finite number of appropriately assumed straight lines passing the point (x1, y1, z1) and the sphere Q, the C-arm 103 is moved and positioned such that the position of the imaging surface center of the X-ray detector 106 is consistent with a point (em, fm, gm) (m=1, 2, . . . , or n) closest to the point (ec, fc, gc) (i.e., such that (ec, fc, gc)=(em, fm, gm)). By this method, "only" the rotations indicated by the arrows C and D in FIG. 7 need to be performed as the movement of the C-arm 103 by assuming the sphere Q. In addition, this movement can approximately satisfy equation (5) with the shortest distance.

Another practical method is as follows. That is, on the basis of the coordinate values (ec, fc, gc) of the center of the X-ray detector 106 at the present time (=without moving the C-arm 3), the known coordinate values (x1, y1, z1) are changed to, e.g., (x1, y1+Δ1, Δ1, z1+Δ2) (note that −10 cm≤Δ1 or Δ2)≤10 cm). Δ1 and Δ2 by which a vector B (corresponding to vector Ax=(ax, bx, cx) in equation (5)) defined by (x1, y1+Δ1, z1+Δ2) and (ec, fc, gc) (=(e0, f0, g0)) is consistent with or approximated to the vector A in equation (3). It is obvious that only the table top 102b needs to be moved in this method.

As the "limitations" described above, it is also possible to impose conditions expressed by, e.g., "the enlargement ratio of the fluoroscopic image DZ on the image displaying unit D is not changed" and "only the vertical movement of the bed 102 is adjusted".

In either case, the bed 102 and/or the C-arm 103 is properly positioned to satisfy equation (5) by the above calculations. Consequently, an image of the region of interest SPR is displayed in the center of the image displaying unit D. That is, "adjustment" described at the beginning of this first method is automatically, rapidly, and efficiently performed. Accordingly, the first method of this second mode can reduce the exposure dose of the patient without forcing any unwanted exposure to X-rays, as in the first mode mentioned earlier.

(Second Method)

The gist of this second method is to improve the positioning accuracy of the above first method. That is, the precondition of the first method is to apply appropriate approximation in each processing. Therefore, it is not always possible to display an image of the region of interest SPR in the center of the image displaying unit D only by practicing calculations once. This event can generally occur especially because the preset value dt introduced in the above explanation is originally a value which is determined relatively roughly.

Accordingly, the object of this second method is to further improve the accuracy of the "adjustment" on the basis of the results obtained by the above first method. More specifically, similar to the above first method, an input for specifying the region of interest SPR in a fluoroscopic image DZ' (not shown) acquired by the bed 102 and the C-arm 103 moved and positioned to have a new relative positional relationship is performed on the basis of the calculation results in the first method. As a consequence, an expression equivalent to equation (1), i.e., $$(x,y,z)=(a1,b1,c1)\cdot t1+(e',f',g') \quad (6)$$

is obtained. The meanings of vector A1=(a1, b1, c1) and coordinate values (e', f', g') are the same as in equation (1). For example, the coordinate values (e', f', g') are those coordinate values on the real space on the X-ray detector 106, which correspond to a region specified by the input currently performed. The "region specified by the input" is the "central region SPC" in the first method and can be regarded as the same region in this second method.

By simultaneously solving equation (6) thus obtained and equation (1), new coordinate values (x1', y1', z1') of the region of interest SPR can be calculated. Since the influence of the preset value dt is eliminated, the coordinate values (x1', y1', z1') are obtained independently of the preset value dt. After that, as described above with reference to step U5 in FIG. 13, the bed 102 and/or the C-arm 103 is moved and positioned again. From the foregoing, this second method can display an image of the region of interest SPR more accurately in the center of the image displaying unit D.

(Third Method)

This third method is an application of the first and second methods described above. That is, the bed 102 and/or the C-arm 103 is moved and positioned, without using the preset value dt, such that the region of interest SPR is projected onto the center of the X-ray detector 106 from the beginning.

Figure 16:
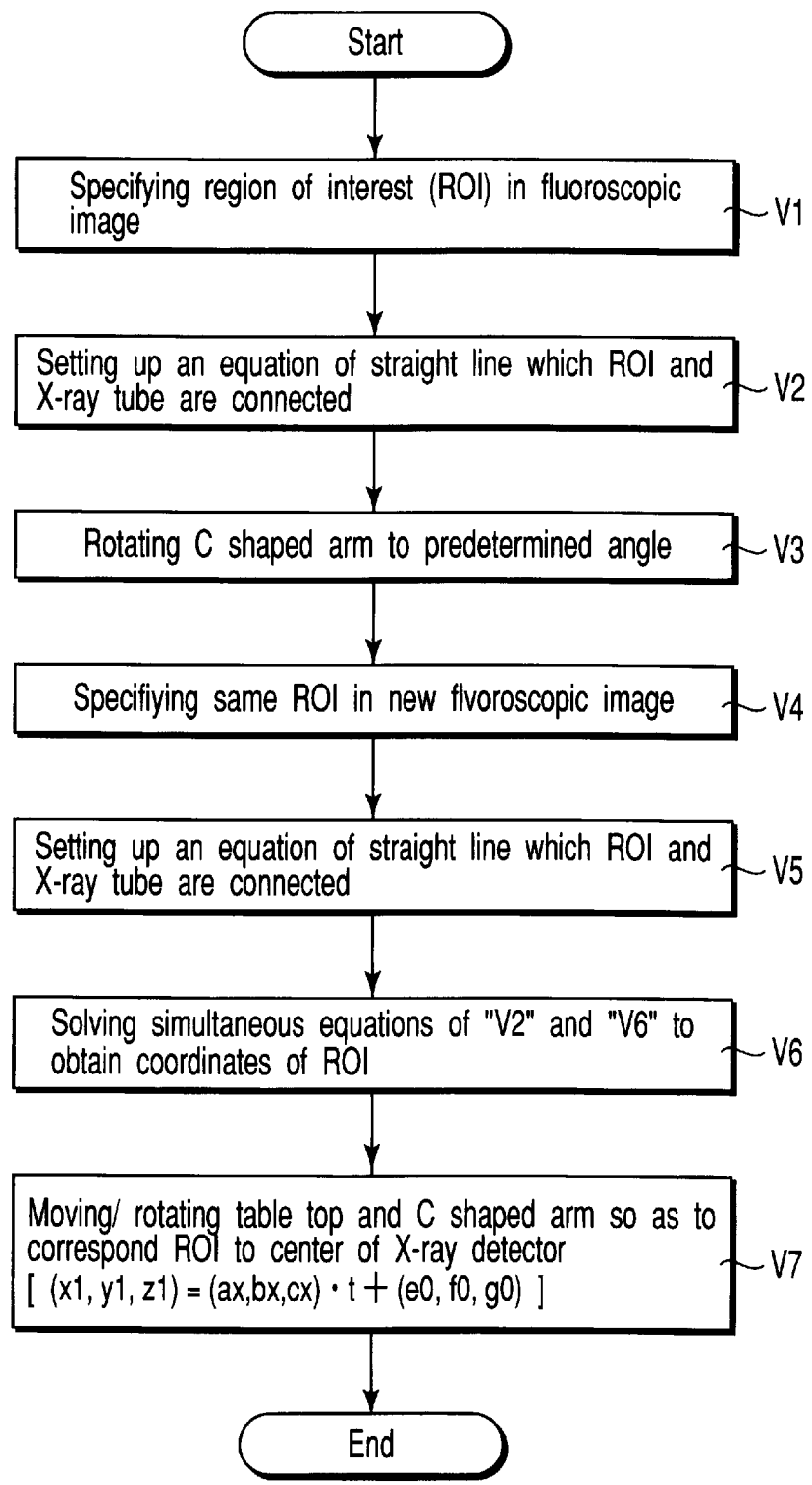
FIG. 16 is a flow chart showing the flow of a process according to the second method of the second mode of the second embodiment, by which on the basis of an input for specifying a region of interest in a fluoroscopic image, an image of this region of interest is displayed in the center of the image displaying unit.

First, an input for specifying the region of interest SPR in a given fluoroscopic image acquired is performed via the input device 74, and an expression of the X-ray focus passing this region of interest SPR is obtained (steps V1 and V2 in FIG. 16). In this respect, the processing is exactly the same as in the first method. As a consequence, an equation equivalent to equation (1) is obtained. For the sake of descriptive convenience, the vector A and the coordinate values (e, f, g) in equation (1) are replaced with vector Aa=(aa, ba, ca) and (ea, fa, ga), respectively (their essential qualities, of course, remain unchanged).

$$(x,y,z)=(aa,ba,ca)\cdot t+(ea,fa,ga) \quad (1)'$$

Next, as indicated in step V3 of FIG. 16, the control unit C automatically changes the angle of the C-arm 103 by a predetermined amount, and obtains a fluoroscopic image DZ" (not shown) again after that. As indicated in steps V4 and V5 of FIG. 16, the control unit C specifies the region of interest SPR in this new fluoroscopic image DZ" again via the input device 74, thereby obtaining an expression of the X-ray locus passing this region of interest SPR again. That is, assuming that a coordinate point, on the real space on the X-ray detector 106, corresponding to a region related to specification inputting in this case is (eb, fb, cb), and that a vector connecting this coordinate point (eb, fb, gb) and the center of the X-ray tube 105 is vector Ab=(ab, bb, cb), $$(x,y,z)=(ab,bb,cb)\cdot t1+(eb,fb,gb) \quad (7)$$

is obtained.

Figure 17:
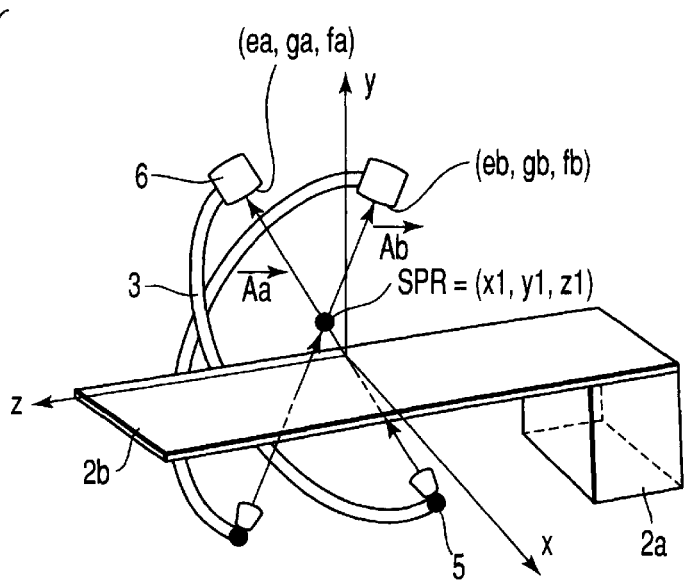
FIG. 17 is a view for explaining a three-dimensional space, X-ray locus, and the like assumed in practicing the process shown in FIG. 16.

The result is shown in FIG. 17. Referring to FIG. 17, two X-ray loci passing the region of interest SPR are obtained by the above operation (of changing the angle of the C-arm 103 by a predetermined amount) (note that this situation in FIG. 17 applies to illustration of equations (1) and (6) in the second method). After that, similar to the second method described above, equations (1)' and (7) are simultaneously solved to obtain coordinate values (x1, y1, z1) of the region of interest SPR (step V6 in FIG. 16). Subsequently, in the same manner as in the above first method, the bed 102 and/or the C-arm 103 is moved and positioned such that the region of interest SPR having these coordinate values (x1, y1, z1) can be projected onto the center of the X-ray detector 106 (step V7 in FIG. 16).

As is apparent from the above explanation, in this third method, the preset value dt is unnecessary from the beginning. Accordingly, the effect aimed in the above second method can be obtained from the beginning.

Note that the following form of application can be used in this second mode. That is, after the region of interest SPR is once displayed in the center of the image displaying unit D through the processes in the first, second, and third methods described above, it is possible to maintain this display of the region of interest SPR in the center even when the user of the apparatus directly issues a command for moving the bed 102 (table top 102*b*) and the C-arm 103 via the input device 74 (movement by manual operation). More specifically, when a manual operation like this is performed, the display position of an image of the region of interest SPR on the image displaying unit D is generally changed (deviates from the center). To cancel this change, the bed 102 and/or the C-arm 103 is automatically moved and positioned.

To this end, a new expression in the form of equation (5) by which a displacement (given as (x1+Δx, y1+Δy, z1+Δz) if the displacement is the movement of the bed 102, or as (e0+Δe, f0+Δf, g0+Δg) if the displacement is the movement or rotation of the C-arm 103) caused by the amount given by the above manual operation is canceled need only be obtained by the procedure as described in the first method, on the basis of the vector Ax=(ax, bx, cx) and the coordinate values (x1, y1, z1) and (e0, f0, g0) defined in the form of equation (5).

(Third Mode)

The method of use, of this angiographic apparatus 101, related to both the first and second modes described above will be explained below. The "method of use" "related to both" means that the angiographic apparatus 101 according to this mode is used in the form of a so-called combination of the principal concept (imaging position information) in the first mode and the principal concept "input for specifying a region of interest" in the second mode. Details will be described below.

In the third method of the second mode, an input is performed to specify the region of interest SPR in each of two fluoroscopic images acquired. On the basis of this, the bed 102 and/or the C-arm 103 is properly moved and positioned such that this region of interest SPR is projected onto the center of the X-ray detector 106, i.e., an image of the region of interest SPR is displayed in the center of the image displaying unit D.

During the execution of an inspection, it is naturally possible that an already sensed fluoroscopic image (=a fluoroscopic image already stored in the image memory M) containing an image of the region of interest SPR is acquired before the use of the third method is practiced. Also, this fluoroscopic image data file is related to an imaging position data file as described in the first method.

Accordingly, when a fluoroscopic image like this is present and this fluoroscopic image is acquired in an imaging position different from the imaging position of a fluoroscopic image acquired at that time, the step (V3 in FIG. 16) of changing the angle of the C-arm 103, necessary to acquire the second fluoroscopic image, can be omitted in the third method of the second mode. This is so because an expression equivalent to equation (7) can be obtained from an imaging position data file related to the sensed fluoroscopic image data file. In this case, however, unlike in the first mode described earlier, the step is not so simple as to move the bed 102 and/or the C-arm 103 by using imaging position information "itself" attached to the selected image. That is, the steps (from step V4 in FIG. 16) after the input for specifying a region of interest in the image are of course necessary.

This similarly applies to the first and second methods of the second mode. That is, in these first and second methods, the fluoroscopic image DZ or DZ' required in the processes of these methods is unnecessary in some cases, i.e., when an already sensed fluoroscopic image which includes an image of the region of interest SPR and which can replace the fluoroscopic image DZ or DZ' is present.

An imaging position data file related to an image data file as described above can also be effectively used in the second mode. This can further reduce the exposure dose of the patient compared to each method of the second mode.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An X-ray diagnosis apparatus comprising:
    an X-ray tube;
    an imaging system which detects X-rays emitted from said X-ray tube and transmitted through an object to be examined, and generates X-ray image data;
    an arm which supports said X-ray tube and said imaging system;
    an arm support mechanism which rotatably and movably supports said arm;
    a bed which holds the object between said X-ray tube and said imaging system;
    a three-dimensional image generating unit which generates three-dimensional image data from volume data concerning the object;
    a display unit which displays the three-dimensional image data;
    an input device which designates an interest point on the displayed three-dimensional image data; and
    a controller which controls at least one of said arm support mechanism and said bed, such that the center of the X-ray image data generated by said imaging system is positioned on a portion of the object which substantially corresponds to the designated interest point,
    wherein in order to match a second coordinate system of the volume data with a first coordinate system of said X-ray diagnosis apparatus, said controller calculates a vector shift of the three-dimensional coordinates, expressed on the second coordinate system, of a point on a specific portion in the three-dimensional image, with respect to the three-dimensional coordinates, expressed on the first coordinate system, of a point on the same specific portion in the X-ray image.

2. An apparatus according to claim 1, wherein said controller converts the three-dimensional coordinates of the interest point expressed on the second coordinate system into three-dimensional coordinates expressed on the first coordinate system, on the basis of the vector shift.

3. An apparatus according to claim 2, wherein said controller calculates a moving vector of a rotation central point of said arm with respect to the converted three-dimensional coordinates.

4. An apparatus according to claim 3, wherein said controller controls said arm support mechanism to move said arm on the basis of the calculated moving vector.

5. An apparatus according to claim 1, wherein the volume data is generated by an external image diagnosis apparatus.

6. An apparatus according to claim 1, further comprising an image generating unit which reconstructs the volume data on the basis of X-ray image data obtained by imaging in a plurality of directions by said imaging system.

7. An apparatus according to claim 1, further comprising an X-ray image display unit which displays the X-ray image data at substantially the same magnification as the three-dimensional image data.

8. An apparatus according to claim 1, further comprising an image processing unit which enlarges the X-ray image data at substantially the same magnification as the three-dimensional image data.

9. An X-ray diagnosis apparatus comprising:
    an X-ray tube;
    an imaging system which detects X-rays emitted from said X-ray tube and transmitted through an object to be examined, and generates X-ray image data;
    an arm which supports said X-ray tube and said imaging system;
    an arm support mechanism which supports said arm such that said arm can rotate around a plurality of rotation central axes and can also move;
    a bed which holds the object between said X-ray tube and said imaging system;
    a three-dimensional image generating unit which generates three-dimensional image data from volume data concerning the object;
    a display unit which displays the three-dimensional image data;

an input device which designates an interest point on the displayed three-dimensional image data; and a controller which controls at least one of said arm support mechanism and said bed, such that the intersection of the plurality of rotation central axes is positioned on a portion of the object which corresponds to the designated interest point;

wherein in order to match a second coordinate system of the volume data with a first coordinate system of said X-ray diagnosis apparatus, said controller calculates a vector shift of the three-dimensional coordinates, expressed on the second coordinate system, of a point on a specific portion in the three-dimensional image, with respect to the three-dimensional coordinates, expressed on the first coordinate system, of a point on the same specific portion in the X-ray image.

10. An apparatus according to claim 9, wherein said controller converts the three-dimensional coordinates of the interest point expressed on the second coordinate system into three-dimensional coordinates expressed on the first coordinate system, on the basis of the vector shift.

11. An apparatus according to claim 10, wherein said controller calculates a moving vector of the three-dimensional coordinates of the intersection of the plurality of rotation central axes with respect to the converted three-dimensional coordinates.

12. An apparatus according to claim 11, wherein said controller controls said arm support mechanism to move said arm on the basis of the calculated moving vector.

13. An apparatus according to claim 9, wherein the volume data is generated by an external image diagnosis apparatus.

14. An apparatus according to claim 9, further comprising an image generating unit which reconstructs the volume data on the basis of X-ray image data obtained by imaging in a plurality of directions by said imaging system.

15. An apparatus according to claim 9, further comprising an X-ray image display unit which displays the X-ray image data at substantially the same magnification as the three-dimensional image data.

16. An apparatus according to claim 9, further comprising an image processing unit which enlarges the X-ray image data at substantially the same magnification as the three-dimensional image data.

* * * * *